United States Patent [19]
Dodge et al.

[11] Patent Number: 5,808,061
[45] Date of Patent: Sep. 15, 1998

[54] INTERMEDIATES AND PROCESSES FOR PREPARING BENZOTHIOPHENE COMPOUNDS

[75] Inventors: Jeffrey A. Dodge, Indianapolis; Mark G. Stocksdale, Fishers, both of Ind.

[73] Assignee: Eli Lilly and Company, Indianapolis, Ind.

[21] Appl. No.: 503,444

[22] Filed: Jul. 17, 1995

Related U.S. Application Data

[63] Continuation of Ser. No. 220,853, Mar. 31, 1994, abandoned.

[51] Int. Cl.[6] .................. C07D 333/56; C07D 409/00; C07D 413/00; C07D 403/00
[52] U.S. Cl. ................... 540/602; 544/144; 544/146; 546/202; 548/525; 549/57
[58] Field of Search ............... 546/202; 544/144, 544/146; 549/57; 548/525; 540/602

[56] References Cited

U.S. PATENT DOCUMENTS

| | | | |
|---|---|---|---|
| 4,133,814 | 1/1979 | Jones et al. | 260/326.55 |
| 4,380,635 | 4/1983 | Peters | 546/202 |

OTHER PUBLICATIONS

Draper, et al., "Effects of Raloxifene (LY139481 HC1) on Biochemical Markers of Bone and Lipid Metabolism in Healthy Postmenopausal Women", Hong Kong, Fourth Int'l Symp. on Osteoporosis, Mar. 29, 1993.

Kym et al, Chemical Abstract vol. 11d No. 270,262 "Molecular Structure" 1993.

*Primary Examiner*—Alan L. Rotman
*Assistant Examiner*—Raymond Covington
*Attorney, Agent, or Firm*—Janelle D. Strode; David E. Boone

[57] ABSTRACT

The present invention provides a novel process for preparing a compound of formula I

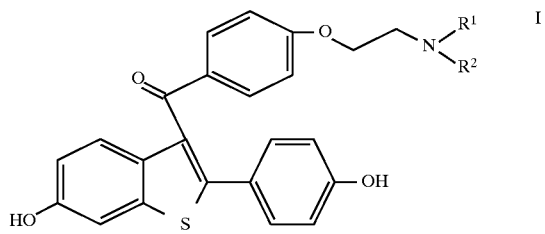

wherein $R^1$ and $R^2$ combine to form $C_4$–$C_6$ polymethylene, —$CH_2CH(CH_3)CH_2CH_2$—, —$CH_2C(CH_3)_2CH_2CH_2$—, or —$CH_2CH_2OCH_2CH_2$—; or a pharmaceutically acceptable salt or solvate thereof.

Also provided intermediates of formulae II and IV

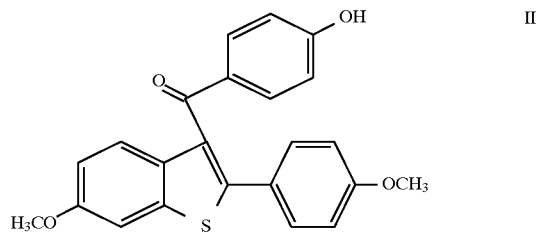

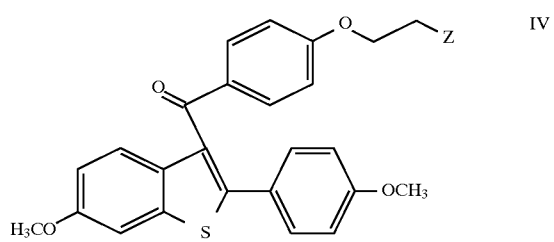

wherein Z is a leaving group.

15 Claims, No Drawings

INTERMEDIATES AND PROCESSES FOR PREPARING BENZOTHIOPHENE COMPOUNDS

This application is a continuation of prior application Ser. No. 08/220,853, filed on Mar. 31, 1994 now abandoned.

FIELD OF THE INVENTION

This invention relates to the fields of pharmaceutical and organic chemistry and provides novel intermediates and processes for preparing certain benzothiophene compounds useful, inter alia, for the treatment of osteoporosis in postmenopausal women.

BACKGROUND OF THE INVENTION

Compounds of formula I

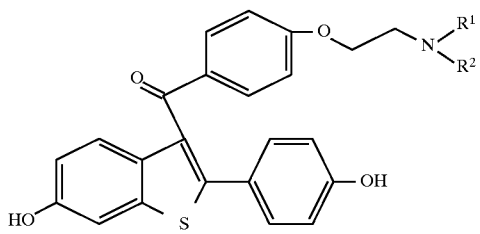

wherein
$R^1$ and $R^2$ combine to form $C_4$–$C_6$ polymethylene, —$CH_2CH(CH_3)CH_2CH_2$—, —$CH_2C(CH_3)_2CH_2CH_2$—, or —$CH_2CH_2OCH_2CH_2$—; or a pharmaceutically acceptable salt or solvate thereof, are known as antifertility agents (see, e.g., U.S. Pat. No. 4,133,814) as well as agents which are useful for the treatment of postmenopausal osteoporosis (see, e.g., Draper, et al., *Effects of Raloxifene* (LY139481 HCl) *on Biochemical Markers of Bone and Lipid Metabolism in Health Postmenopausal Women,* Hong Kong, Fourth Int'l. Symp. on Osteoporosis, Mar. 29, 1993). Raloxifene is a compound of formula I in which $R^1$ and $R^2$ are combined to form $C_5$ polymethylene.

Jones and Suarez, in U.S. Pat. No. 4,133,814, supra, first taught the compounds prepared by the present invention, and showed a number of processes for preparing them. In general, Jones, et al., as well as Peters, M. K. (U.S. Pat. No. 4,380,635), prepare benzothiophenes of formula I via the acylation of a compound of formula V

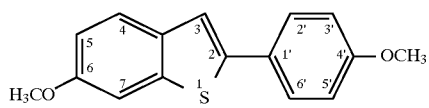

with a compound of formula VI

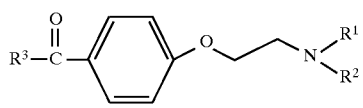

wherein $R^3$ is chloro or bromo and $R^1$ and $R^2$ are as defined above, and the 6- and 4'-position hydroxy protecting groups are removed via standard procedures.

One aspect of the present invention provides novel processes for preparing compounds of formula I.

Another aspect of the present invention provides novel intermediates which are useful for preparing compounds of formula I.

SUMMARY OF THE INVENTION

The present invention provides a process for preparing a compound of formula I

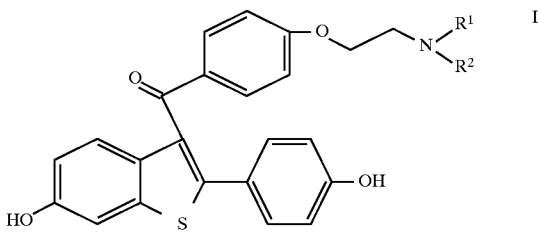

wherein
$R^1$ and $R^2$ combine to form $C_4$–$C_6$ polymethylene, —$CH_2CH(CH_3)CH_2CH_2$—, —$CH_2C(CH_3)_2CH_2CH_2$—, or —$CH_2CH_2OCH_2CH_2$—; or a pharmaceutically acceptable salt or solvate thereof, comprising
a) reacting a compound of formula II

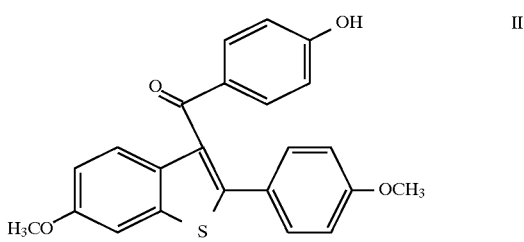

with a compound of formula III

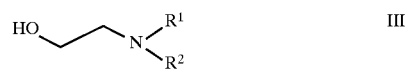

wherein $R^1$ and $R^2$ are as defined above, in the presence of triphenylphosphine and diethyl azodicarboxylate; or
b) reacting a compound of formula II

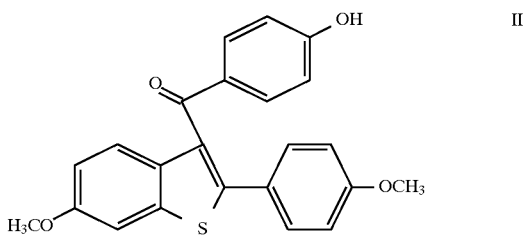

with a compound of the formula Z—$CH_2$—$CH_2$—Z in which Z is the same or different leaving group, and reacting the resulting compound of formula IV

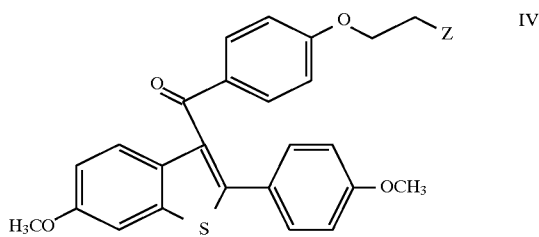

wherein Z is a leaving group, with pyrrolidine, piperidine, hexamethyleneimine, methylpyrrolidine, dimethylpyrrolidine, or morpholine;
c) deprotecting the 6- and 4'-position hydroxy group of the reaction product of step a) or step b); and
d) optionally salifying or forming a solvate of the reaction product of step c).

Also provided by the present invention is a compound of formula II

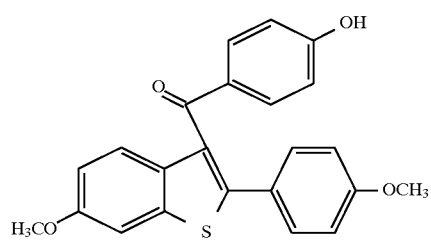

and compounds of formula IV

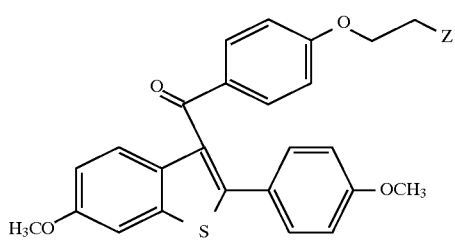

wherein Z is a leaving group.

DETAILED DESCRIPTION OF THE INVENTION

The present invention provides a convenient process for preparing benzothiophenes of formula I.

The starting material for the process of the present invention, a compound of formula II, is prepared via known procedures using known or commercially available materials. In general, a compound of formula V, supra, which is described by Peters, M. K. in U.S. Pat. No. 4,380,635, is acylated with anisoyl chloride in the presence of an appropriate catalyst and an inert solvent. U.S. Pat. No. 4,380,635 is herein incorporated by reference.

The acylation step of the present process, in which a compound of formula VI is prepared (see Scheme I, infra), is a Friedel-Crafts reaction, and is carried out in the usual manner, using an appropriate catalyst such as, for example, aluminum chloride or bromide, gallium dichloride or trichloride, molydenum pentachloride, iron chloride, and the like [see, e.g., Olah, G. A., et al., *J. Am. Chem. Soc.*, 94:7448 (1974)], in the presence of an inert solvent. Of these catalysts, aluminum chloride is preferred.

Appropriate inert solvents include, for example, halogenated solvents such as dichloromethane, 1,2-dichloroethane, chloroform, and the like, as well as aromatics such as benzene, chlorobenzene, and the like. Of these, a halogenated solvent, especially 1,2-dichloroethane, is preferred.

It has been found that toluene is rather easily acylated under the conditions used in the Friedel-Crafts reaction. It, therefore, is important to remove any previously used toluene so that waste of the acylating agent is avoided.

The above acylation may be carried out at temperatures from about –30° C. to about 100° C., preferably in the range from about –10° C. to about 20° C.

It generally is preferred that an equimolar amount of each substrate is reacted together. However, it is preferred that an excess of anisoyl chloride is used for this reaction.

The acylation step is rapid, taking from about 15 minutes to a few hours when run at the preferred temperature range. Longer reaction times may be used, but usually are not advantageous.

Next, the methyl hydroxy protecting group of the benzoyl moiety of a formula VI compound is selectively removed via standard procedures. Typically, the formula VI compound is reacted with the lithium or, preferably, the sodium salt of ethanethiol, essentially as described in Preparation 2, infra.

This reaction is performed in a non-reactive solvent such as N,N-dimethylformamide and the like. The reaction is performed at temperatures from about 50° C. to about 120° C. and allowed to run until compounds of formula II are prepared. The reaction typically takes about 4 hours when run at 80° C. However, the progress of the reaction may be monitored by using standard chromatographic techniques.

The formula II compound is novel and useful as the starting material for the processes of the present invention.

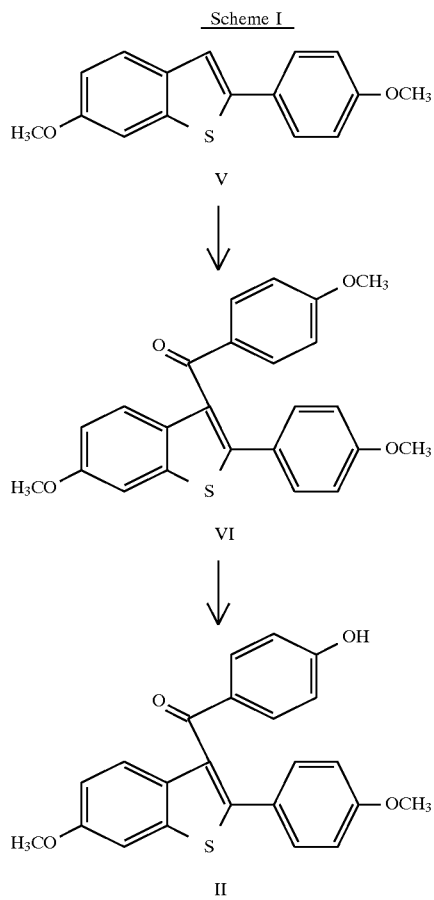

Scheme I

The process of the present invention is represented below in Scheme II.

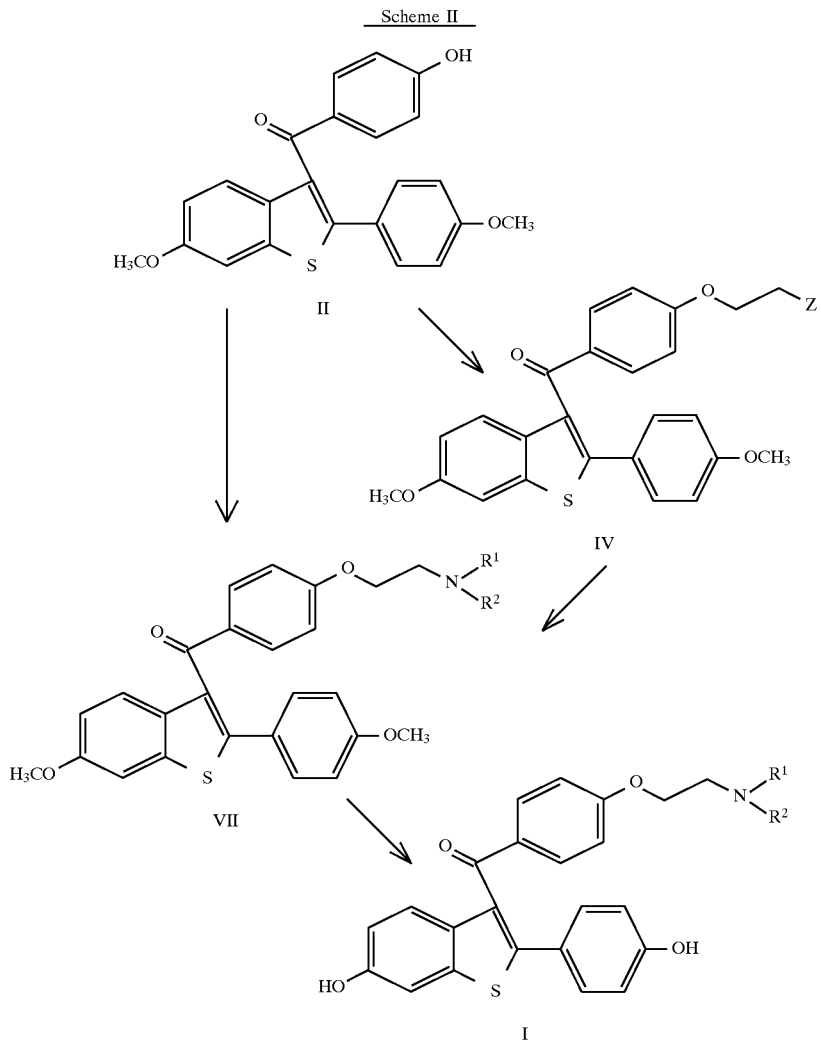

wherein $R^1$, $R^2$, and Z are as defined above, or a salt thereof.

The first step of the preferred process of the present invention involves reacting the formula II compound with a compound of formula III

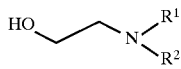   III wherein $R^1$ and $R^2$ are as defined above, in the presence of triphenylphosphine, diethyl azodicarboxylate (DEAD), and an appropriate solvent, resulting in a compound of formula VII above. This process is known in the art as a Mitsunobo coupling.

Although this coupling can be accomplished using various concentrations of the reactants and reagents, it is best to use 1 to 2 equivalents of a formula III compound, triphenylphosphine, and DEAD per each equivalent of formula II compound used.

This reaction also is best carried out in the presence of an inert solvent such as, for example, toluene, benzene, or, preferably tetrahydrofuran. The reaction is performed at temperatures from about 0° C. to about 40° C., preferably at ambient temperature, until a formula VII compound is prepared. Typically, the reaction takes about 18 hours when run at ambient temperature, but the progress of the reaction can be monitored via standard chromatographic techniques.

A preferred formula III reactant, and thus, providing a compound of formula VII, is that in which $R^1$ and $R^2$ combine to form $C_4$–$C_6$ polymethylene, particularly $C_5$ polymethylene. The term "$C_4$–$C_6$ polymethylene" refers to tetramethylene, pentamethylene, and hexamethylene.

Following preparation of a formula VII compound, the 6- and 4'-position protected hydroxy groups are demethylated via procedures known by one of ordinary skill in the art.

Generally, deprotection (demethylation) is accomplished by the addition of a sulfur compound and a lewis acid, preferably aluminum chloride, to the reaction mixture remaining from the preparation of formula VII compounds.

The sulfur compound, preferably, are the alkylthiols such as methanethiol, isopropropanethiol, butanethiol, ethanethiol, the preferred agent, and the like, dialkyl sulfides such as, for example, butyl s-butyl sulfide, ethyl propyl sulfide, butyl isopropyl sulfide, dimethyl sulfide, methyl ethyl sulfide, and the like, benzenethiol, methionine, and alkyl phenyl sulfides such as, for example, methyl phenyl sulfide, ethyl phenyl sulfide, butyl phenyl sulfide, and the like.

It has been found that the demethylation step is best carried out when a substantial excess of the sulfur compound and the lewis acid is used, in the range from about 4 to about 10 moles per mole of substrate. The process can be carried out, although less efficiently, with a smaller amount of the sulfur compound, in the range from about 2 to 3 moles per mole of substrate. It is also possible to use a small amount of the sulfur compound, such as 2 to 3 moles per mole of substrate, and to improve the yield by the addition of about 1 to 3 moles of an alkali metal halide such as sodium, potassium, or lithium chloride, iodide, or bromide.

This demethylation reaction runs well, and is preferred, when run at ambient temperature, in the range from about 15° C. to about 30° C. However, the demethylation step may be carried out at temperatures in the range from about −30° C. to about 50° C. Short reaction times, about 1 hour, have been found to be adequate.

After a compound of formula VII has been demethylated, forming a compound of formula I, it is recovered and isolated by conventional means. The examples below further illustrate such recovery and isolation.

The above-described process can be carried out in two, isolated steps in which the product of the first step is recovered, isolated, and purfied prior to carrying out the demethylation step. However, the present process also may be carried out in the same vessel without purificatin of intermediates, thus providing a one-pot process.

As an alternative to the above-described process, a formula II compound is first alkylated with a compound of the formula Z—CH$_2$—CH$_2$—Z, in which each Z is the same or different leaving group, in the presence of an alkali solution, and reacting the product of the first step with pyrrolidine, piperidine, hexamethyleneimine, methylpyrrolidine, dimethylpyrrolidine, or morpholine. The reaction product from this amine addition step is then demethylated to provide a compound of formula I (see, Scheme II, supra).

First, the phenol moiety of the formula II compound is converted to an ether moiety via procedures known in the art. Typically, an excess of the alkylating agent (Z—CH$_2$—CH$_2$—Z) is reacted with the formula II compound in an alkali solution.

Appropriate alkylating agents, in which each Z is the same or different leaving group, include, for example, the sulfonates such as methansulfonate, 4-bromobenzenesulfonate, toluenesulfonate, ethanesulfonate, isopropanesulfonate, 4-methoxybenzenesulfonate, 4-nitrobenzenesulfonate, 2-chlorobenzenesulfonate, triflate, and the like, halogens such as bromo, chloro, iodo, and the like, and other related leaving groups. Because bromo is preferred, the preferred alkylating agent is 1,2-dibromoethane. This alkylation is carried out by using at least 2 equivalents, and preferably greater than 2 equivalents, of alkylating agent per equivalent of substrate.

In an alkali solution, the phenol moiety exists as a phenoxide ion which displaces one of the leaving groups of the alkylating agents. A preferred alkali solution contains potassium carbonate in an inert solvent such as, for example, methylethyl ketone or dimethylformamide.

This reaction is best run when the alkali solution containing the reactants and reagents is brought to reflux and allowed to run to completion. When using methylethyl ketone as the preferred solvent, reaction times run from about 6 hours to about 20 hours.

The reaction product from the first step, a novel compound of formula IV, is then reacted with pyrrolidine, piperidine, hexamethyleneimine, methylpyrrolidine, dimethylpyrrolidine, or morpholine, forming a compound of VII, via standard techniques. Preferably, the hydrochloride salt of piperidine is reacted with the formula IV compound in an inert solvent, such as anhydrous dimethylformamide, and heated to a temperature range from about 60° C. to about 110° C. When the mixture is heated to a preferred temperature of about 90° C., the reaction only takes about 30 minutes to about 1 hour. However, changes in the reaction conditions will influence the amount of time this reaction needs to be run to completion. Of course, the progress of the reaction can be monitored via standard chromatographic techniques.

Once this reaction is completed, the resulting formula VII compound is demethylated according to the above-described process, forming a compound of formula I.

Although the reaction product from each step of the present process can be recovered and isolated via standard techniques, each step of this process can be carried out in a single vessel, providing a one-pot process.

Although the free-base form of formula I compounds can be used for various medicinal indications, it is preferred to prepare and use a pharmaceutically acceptable salt form. Thus, compounds of formula I optionally form pharmaceutically acceptable acid and base addition salts with a wide variety of organic and inorganic acids and bases, and include the physiologically acceptable salts which are often used in pharmaceutical chemistry. Preparation of such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzene sulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts and solvates, the latter of which are prepared by methods well known to one of ordinary skill in the organic chemical arts, generally have enhanced solubility characteristics compared to the compound from which they are derived, and thus are often more amenable to formulation as liquids or emulsions.

The following examples are presented to further illustrate the preparation of compounds of the present invention. It is not intended that the invention be limited in scope by reason of any of the following examples.

The terms "NMR", "IR" or "MS" following a synthesis protocol indicates that the nuclear magnetic resonance spectrum, infrared spectrum, or the mass spectrometry was performed and was consistent with the title product.

Preparation 1

6-methoxy-2-(p-methoxyphenyl)benzo[b]thien-3-yl p-methoxyphenyl ketone

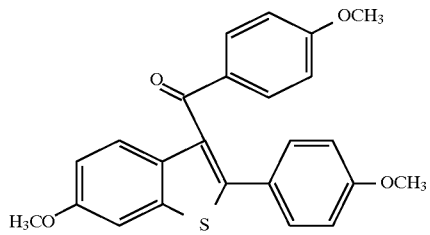

VI

To a solution of p-anisoyl chloride (1.54 g, 9.00 mmol) stirring at ambient temperature in anhydrous methylene chloride (100 ml) was added 6-methoxy-2-(4-methoxyphenyl)benzo [b]thiophene (1.62 g, 6.00 mmol). The resulting mixture was cooled to 0° C. and aluminum chloride (1.20 g, 9.00 mmol) was added in small portions over a five minute period. After 1 hour, the reaction mixture was poured into ice water (150 mL) and extracted with methylene chloride. The combined organic extracts were washed with 1N sodium hydroxide, water, brine, dried (magnesium sulfate), filtered, and concentrated. The resulting material was purified by flash chromatography (silica gel, 30% ethyl acetate in hexanes) giving 2.25 g (93%) of a the desired product as a light yellow solid. The product was further purified by recrystallization from acetone/methanol to give 2.11 g (87%): $^1$H NMR (300 MHz, DMSO-$d_6$) δ 7.64–7.69 (m,3H), 7.29–7.32 (m, 3H). 6.86–7.00 (m, 5H), 3.83 (s, 3H) 3.76 (s, 3H); $^{13}$C NMR (75.5 MHz, DMSO-$d_6$) δ 192.0, 163.6, 159.5, 157.4, 141.0, 139.4, 133.2, 131.8, 130.0, 129.6, 125.2, 123.3, 115.0, 114.4, 114.1, 105.1, 55.5, 55.1; IR (CHCl$_3$) 3020, 3015, 2970, 2940, 2840, 1600, 1475, 1253, 1218, 1167; MS (FD) 404 (M+); Anal. Calcd for $C_{24}H_{20}O_4S$: C, 71.27; H, 4.98; S, 7.93; O, 15.82. Found: C, 71.50; H, 5.00; S, 7.98; O, 15.77.

EXAMPLE 1

(4-hydroxyphenyl)[6-methoxy-2-(4-methoxyphenyl) benzo[b]thien-3-y]methano

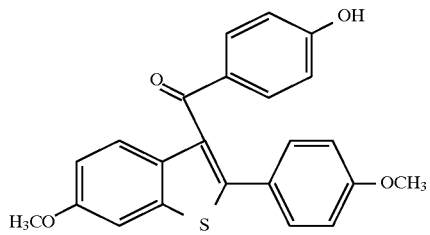

II

To a solution of 6-methoxy-2-(p-methoxyphenyl) benzo[b]thien-3-yl p-methoxyphenyl ketone (0.40 g, 1.00 mmol) stirring in dimethylformamide (DMF; 2 mL) at ambient temperature was added the sodium salt of ethanethiol (3.0 ml of 0.50M solution in DMF) and the reaction mixture was heated to 80° C. After 4 hours, the reaction was diluted with ethyl acetate, and water was added. The mixture was then neutralized with 1N hydrochloric acid and extracted with ethyl acetate. The combined organic extracts were washed with brine, dried (magnesium sulfate), filtered, and concentrated. The resulting solid was purified by radial chromatography (silica gel, 2 mm, 5% EtOAc in methylene chloride) to give 0.31 g (79%) of the desired product as a yellow foam: $^1$H-NMR (300 MHz, CDCl$_3$) δ 7.70–7.73 (d, 2H, J=8.6 Hz), 7.53 (d, 1H, J=8.5 Hz), 7.31–7.34 (m, 3H), 6.94–6.98 (dd, 1H, J=9.0 Hz, J=2.4 Hz), 6.75 (d, 2H, J=8.7 Hz), 6.67 (d, 2H, J=9.1 Hz), 3.88 (s, 3H), 3.74 (s, 3H); $^{13}$CNMR (75.5 MHz CDCl$_3$) δ 192.9, 159.9, 158.6, 156.5, 141.9, 138.9, 132.7, 131.7, 129.2, 129.1, 128.8, 124.7, 122.8, 114.3, 113.7, 112.9, 103.4, 54.5, 54.1; IR (CHCl$_3$) 3585, 3265, 3022, 3012, 2970, 2940, 2840, 1602, 1476, 1254, 1163; MS (FD+) 390 (M+); Anal. Calcd for $C_{23}H_{18}O_4S$: C, 70.75; H, 4.65. Found: C, 70.93; H, 4.56.

EXAMPLE 2

[6-methoxy-2-(4-methoxyphenyl)benzo[b]thien-3-yl][4-[2-(1-piperidinyl)ethoxy]phenyl]methanone

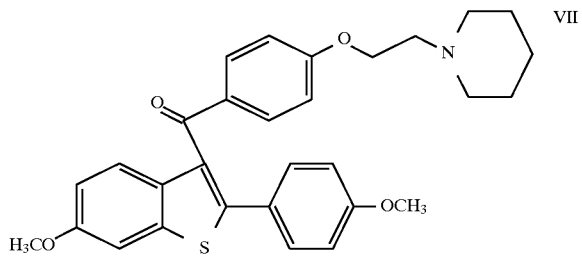

VII

To a solution of 1-piperidineethanol (0.32 g, 2.50 mmol) stirring in anhydrous tetrahydrofuran (20 mL) at ambient temperature was added triphenylphosphine (0.52 g, 2.00 mmol) followed by diethyl azodicarboxylate (2.0 mmol). After 5 minutes, (4-hydroxyphenyl) [b-methoxy-2-(4-methoxyphenylbenzo[b]thien-3-yl]methano (0.39 g, 1.00 mmol) was added to this solution and the mixture stirred for 18 hours at ambient temperature. The reaction mixture was concentrated and the resulting material purified by radial chromatography (silica gel, 4/.1/.1 methylene chloride/ethyl acetate/methanol) to give 0.46 g (91%) the desired product as a yellow solid: $^1$HNMR (300 MHz, CDCl$_3$) δ 7.76 (d, 2H, J=8.8 Hz), 7.52 (d, 1H, J=8.9 Hz), 7.31–7.35 (m, 3H), 6.95 (dd, 1H, J=8.9, 2.3 Hz), 6.74–6.77 (m, 4H), 4.08 (t, 2H, J=6.6 Hz), 3.88 (s, 3H), 3.75 (s, 3H), 2.73 (t, 2H, J=6.6 Hz), 2.44–2.52 (m, 4H), 1.55–1.62 (m, 4H), 1.39–1.46 (m, 2H) ; $^{13}$CNMR (75.5 MHz CDCl$_3$) δ 193.2, 163.0, 159.7, 157.6, 142.5, 140.1, 132.3, 130.6, 130.4, 130.3, 126.0, 124.1, 114.8, 114.2, 114.1, 104.5, 66.3, 57.7, 55.6, 55.2, 55.1, 25.9, 24.1; IR (CHCl$_3$) 3008, 2941, 2854, 2833, 1646, 1599, 1476, 1254, 1167 cm$^{-1}$; MS (FD) 501 (M+).

EXAMPLE 3

[6-methoxy-2-(4-methoxyphenyl)benzo[b]thien-3-yl][4-[2-(1-bromo)ethoxy]phenyl]methanone

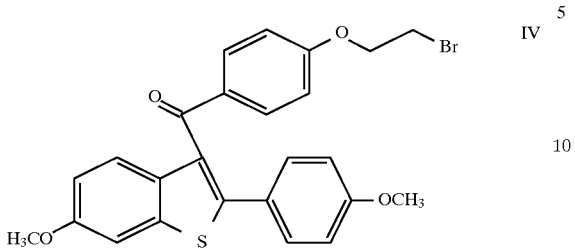

To a solution of (4-hydroxyphenyl) [b-methoxy-2-(4-methoxyphenyl)benzo[b]thien-3-y]methano (3.90 g, 10.0 mmol) stirring in methylethyl ketone (25 mL) was added ground potassium carbonate (2.07 g, 15.0 mmol) followed by 1,2-dibromoethane (10 mL) and the solution brought to reflux. After 18 hours, the reaction mixture was hot filtered and the residue washed thoroughly with ethyl acetate. The filtrate was concentrated and the resulting material purified by flash column chromatography (silica gel, 50% ethyl acetate/hexanes) to give 4.32 g (87%) of desired product as a yellow solid: $^1$H-NMR (300 MHz, CDCl$_3$) δ 7.76 (d, 2H, J=8.8 Hz), 7.55 (d, 1H, 8.9 Hz), 7.31–7.35 (m, 3H), 6.96 (dd, 1H, J=8.9 Hz, J=2.3 Hz), 6.74–6.78 (m, 4H); IR (CHCl$_3$) 3030, 3015, 2965, 2942, 2835, 1601, 1475, 1253, 1240, 1167 cm$^{-1}$; MS (FD+) 496 (M$^+$Br$^{79}$), 498 (M$^+$Br$^{81}$): Anal. calcd. for C$_{25}$H$_{21}$BrO$_4$S: C, 60.37; H, 4.26; Br, 16.07. Found: C, 60.22; H, 4.54; Br, 16.20.

EXAMPLE 4

[6-methoxy-2-(4-methoxyphenyl)benzo[b]thien-3-yl][4-[2-(1-piperidinyl)ethoxy]phenyl]methanone

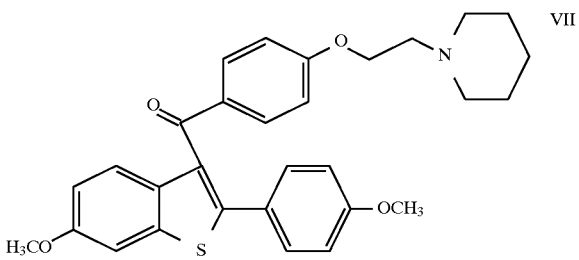

To [6-methoxy-2-(4-methoxyphenyl)benzo[b]thien-3-yl][4-[2-(1-bromo)ethoxy]phenyl]methanone (0.497 g, 1.00 mmol) stirring at ambient temperature in anhydrous DMF (10 mL) was added piperidine (3.00 mmol). The mixture was heated to 90° C. After 45 minutes, the solution was cooled to ambient temperature and water was added. The reaction mixture was extracted with ethyl acetate and the combined organic extracts washed with brine, dried (magnesium sulfate), filtered, and concentrated. The resulting material was purified by radial chromatography (silica gel, 10% MeOH in ethyl acetate) to give 0.47 g (93%) of the desired product as a yellow solid: $^1$HNMR (300 MHz, CDCl$_3$) δ 7.75 (d, 2H, J=8.7 Hz), 7.52 (d, 1H, J=8.9 Hz), 7.31–7.35 (m, 3H), 6.95 (dd, 1H, J=8.9, 2.3 Hz), 6.74–6.77 (m, 4H), 4.08 (t, 2H, J=6.6 Hz), 3.88 (s, 3H), 3.75 (s, 3H), 2.73 (t, 2H, J=6.6 Hz), 2.44–2.52 (m, 4H), 1.55–1.62 (m, 4H), 1.39–1.46 (m, 2H); $^{13}$CNMR (75.5 MHz CDCl$_3$) δ 193.2, 163.1, 160.0, 157.7, 142.2, 140.1, 133.9, 132.3, 130.6, 130.4, 130.3, 126.0, 124.1, 114.8, 114.2, 114.1, 104.5, 66.3, 57.7, 55.6, 55.2, 55.1, 25.9, 24.1; IR (CHCl$_3$) 3008, 2941, 2854, 2834, 1646, 1599, 1476, 1254, 1167 cm$^{-1}$; MS (FD) 502 (M+).

EXAMPLE 5

[6-hydroxy-2-(4-hydroxyphenyl)benzo[b]thien-3-yl][4-[2-(1-piperidinyl)ethoxy]phenyl]methanone hydrochloride

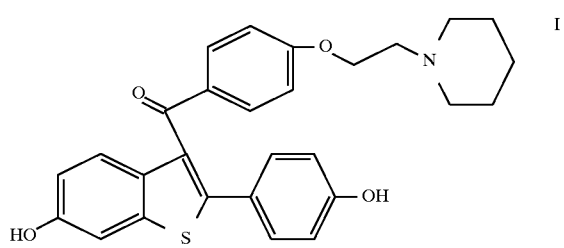

To a 250 ml three-neck round bottom flask are combined 50 mL of ethylene chloride, aluminum trichloride (9.6 q, 72 mmol) and ethanethiol (6.39 q, 103 mmol) to create a pale yellow liquid. To this liquid is added the product of Example 4 (5.0 q, 10.3 mmol) in a gradual fashion. An oil precipitate and the mixture is stirred for about 20 minutes. After cooling the reaction mixture in an ice bath, 100 mL of tetrahydrofuran is added and the mixture is allowed to stir until all of the oil goes into solution.

The reaction mixture is then poured over ice (200 mL) and water (500 mL) and concentrated hydrochloric acid (10 mL) is added. The resulting precipitate (oil) is separated from the liquid by decantation. The liquid is extracted with warm chloroform (2×300 mL). The oil is dissolved by mixing with ethyl acetate, chloroform, sodium bicarbonate, and a small amount of sodium hydroxide. The chloroform extract and the dissolved oil are transferred to a separatory funnel and washed with sodium bicarbonte. The organic phase is then dried over magnesium sulfate and the solvents are removed by evaporation. The resulting product is further purified by high performance liquid chromatography.

We claim:
1. A process for preparing a compound of formula I

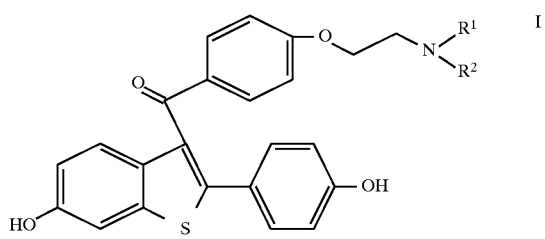

wherein $R^1$ and $R^2$ combine to form $C_4$–$C_6$ polymethylene, —CH$_2$CH(CH$_3$)CH$_2$CH$_2$—, —CH$_2$C(CH$_3$)$_2$CH$_2$CH$_2$—, or —CH$_2$CH$_2$OCH$_2$CH$_2$—; or a pharmaceutically acceptable salt or solvate thereof, comprising a) reacting a compound of formula II

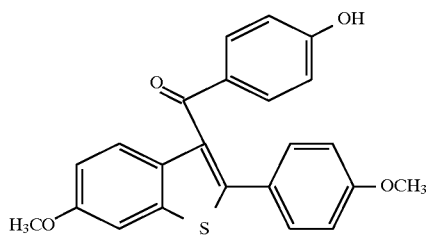

with a compound of formula Z—CH$_2$—CH$_2$—Z in which Z is the same or different leaving group, and reacting the resulting compound of formula IV

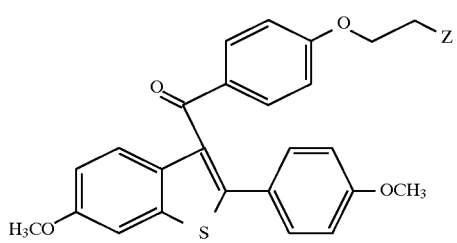

wherein Z is a leaving group, with pyrrolidine, piperidine, hexamethyleneimine, methylpyrrolidine, dimethylpyrrolidine, or morpholine;

b) deprotecting the 6- and 4'-position hydroxy group of the reaction product of step a); and c) optionally salifying or forming a solvate of the reaction product of step b).

2. The process of claim 1 wherein R$^1$ and R$^2$ combine to form C$_4$–C$_6$ polymethylene.

3. The process of claim 2 wherein R$^1$ and R$^2$ combine to form C$_5$ polymethylene.

4. The process of claim 3 wherein said salt thereof is the hydrochloride salt.

5. The process of claim 4 wherein each Z is bromo.

6. The process of claim 1 wherein each Z is bromo.

7. The process of claim 5 which is carried out in a single vessel.

8. The process of claim 1 which is carried out in a single vessel.

9. A process for preparing a compound of formula I

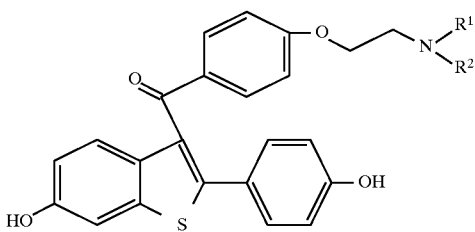

wherein

R$^1$ and R$^2$ combine to form C$_4$–C$_6$ polymethylene, —CH$_2$CH(CH$_3$)CH$_2$CH$_2$—, —CH$_2$C(CH$_3$)$_2$CH$_2$CH$_2$—, or —CH$_2$CH$_2$OCH$_2$CH$_2$—; or a pharmaceutically acceptable salt or solvate thereof, comprising a) reacting a compound of formula II

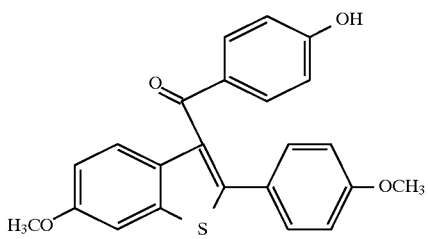

with a compound of formula III

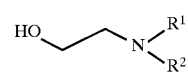

wherein R$^1$ and R$^2$ are as defined above, in the presence of triphenylphosphine and diethyl azodicarboxylate;

b) deprotecting the 6- and 4'-position hydroxy group of the reaction product of step a); and c) optionally salifying or forming a solvate of the reaction product of step b), wherein the process is carried out in a single vessel.

10. The process of claim 9 wherein R$^1$ and R$^2$ combine to form C$_4$–C$_6$ polymethylene.

11. The process of claim 10 wherein R$^1$ and R$^2$ combine to form C$_5$ polymethylene.

12. The process of claim 11 wherein said salt thereof is the hydrochloride salt.

13. A compound of formula IV

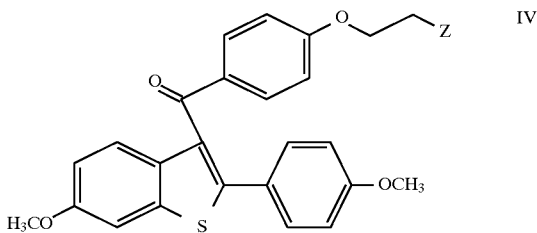

wherein Z is a leaving group.

14. A compound of claim 13 wherein said leaving group is bromo, chloro, or iodo.

15. A compound of claim 14 wherein said leaving group is bromo.

* * * * *